United States Patent
Demkowicz et al.

(10) Patent No.: US 11,939,303 B2
(45) Date of Patent: Mar. 26, 2024

(54) SULFAMATE DERIVATIVES OF 4-(1-PHENYL-1H-[1,2,3]TRIAZOL-4-YL)-PHENOL, DERIVATIVES OF 4-(1-PHENYL-1H-[1,2,3]TRIAZOL-4-YL)-PHENOL, THEIR MEDICAL USE AND THE METHOD OF OBTAINING 4-(1-PHENYL-1H-[1,2,3]TRIAZOL-4-YL)-PHENYL SULFAMATE DERIVATIVES

(71) Applicant: POLITECHNIKA GDANSKA, Gdansk (PL)

(72) Inventors: Sebastian Demkowicz, Gdansk (PL); Mateusz Dasko, Pruszcz Gdanski (PL); Janusz Rachon, Gdansk (PL)

(73) Assignee: Politechnika Gdanska, Gdansk (PL)

( * ) Notice: Subject to any disclaimer, the term of this patent is extended or adjusted under 35 U.S.C. 154(b) by 645 days.

(21) Appl. No.: 17/252,703

(22) PCT Filed: Aug. 20, 2018

(86) PCT No.: PCT/PL2018/000080
§ 371 (c)(1),
(2) Date: Dec. 15, 2020

(87) PCT Pub. No.: WO2019/245393
PCT Pub. Date: Dec. 26, 2019

(65) Prior Publication Data
US 2021/0188785 A1 Jun. 24, 2021

(30) Foreign Application Priority Data
Jun. 18, 2018 (PL) .......................... 425970

(51) Int. Cl.
| C07D 249/06 | (2006.01) |
| A61P 35/00 | (2006.01) |
| G01N 33/573 | (2006.01) |
| A61K 31/4192 | (2006.01) |

(52) U.S. Cl.
CPC ............ *C07D 249/06* (2013.01); *A61P 35/00* (2018.01); *G01N 33/573* (2013.01); *A61K 31/4192* (2013.01)

(58) Field of Classification Search
CPC .... C07D 249/06; A61P 35/00; A61K 31/4192
See application file for complete search history.

(56) References Cited

FOREIGN PATENT DOCUMENTS

| EP | 1193250 | 4/2002 |
| PL | P.425970 | 6/2018 |
| WO | WO 2007/068905 A1 | 6/2007 |
| WO | WO 2009/082398 A1 | 7/2009 |
| WO | WO 2010/015583 A1 | 2/2010 |
| WO | WO 2011/023989 A1 | 3/2011 |
| WO | WO 2015/101670 | 7/2015 |
| WO | PCT/PL2018/000080 | 8/2018 |

OTHER PUBLICATIONS

Nussbaumer et al. "Steroid sulfatase inhibitors," Medicinal Research Reviews, 2004, vol. 24, No. 4, pp. 529-576 (Year: 2004).*
Bey et al. (2008) "Design, synthesis, biological evaluation and pharmacokinetics of bis(hydroxyphenyl) substituted azoles, thiophenes, benzenes, and aza-benzenes as potent and selective nonsteroidal inhibitors of 17beta-hydroxysteroid dehydrogenase type 1 (17beta-HSD1)," J Med Chem 51(21): 6725-6739.
Kaur et al. (2013) "1,4-Diaryl-substituted triazoles as cyclooxygenase-2 inhibitors: Synthesis, biological evaluation and molecular modeling studies," Bioorganic & Medicinal Chemistry 21(14): 4288-4295.
Mohamed Salah et al. (2017) "First Dual Inhibitors of Steroid Sulfatase (STS) and 17β-Hydroxysteroid Dehydrogenase Type 1 (17β-HSD1): Designed Multiple Ligands as Novel Potential Therapeutics for Estrogen-Dependent Diseases," Journal of Medicinal Chemistry 60(9): 4086-4092.
International Search Report and Written Opinion dated Dec. 26, 2019 by the International Search Authority for International Application No. PCT/PL2018/000080, filed on Aug. 19, 2018 and published as WO 2019/245393 on Dec. 26, 2019 (Applicant—Politechnika Gdanska) (10 pages).
International Preliminary Report on Patentability dated Dec. 22, 2020 by the International Search Authority for International Application No. PCT/PL2018/000080, filed on Aug. 19, 2018 and published as WO 2019/245393 on Dec. 26, 2019 (Applicant—Politechnika Gdanska) (7 pages).

* cited by examiner

*Primary Examiner* — Shengjun Wang
(74) *Attorney, Agent, or Firm* — Ballard Spahr LLP

(57) ABSTRACT

The present invention relates to 4-(1-phenyl-1H-[1,2,3]triazol-4-yl)-phenyl sulfamate derivatives and derivatives of 4-(1-phenyl-1H-[1,2,3]triazol-4-yl)-phenol as new compounds. The subject of the invention is the medical use of 4-(1-phenyl-1H-[1,2,3]triazol-4-yl)-phenyl sulfamate derivatives and the medical use of 4-(1-phenyl-1H-[1,2,3] triazol-4-yl)-phenol derivatives. The subject of the invention is the use of new compounds as an agent with the properties of a steroid sulfatase inhibitor and/or an estrogen receptor modulator. The present invention relates to the medical use of novel compounds for use as an antimicrobial medicament and/or estrogen receptor modulator. In particular, 4-(1-phenyl-1H-[1,2,3]triazol-4-yl)-phenyl sulfamate derivatives are for use as medicament in cancer therapy. The invention also relates to a process for the preparation of these new compounds, wherein the derivatives of 4-(1-phenyl-1H-[1,2,3] triazol-4-yl)-phenol are the intermediate product from which the sulfamate derivatives are obtained.

10 Claims, No Drawings

SULFAMATE DERIVATIVES OF 4-(1-PHENYL-1H-[1,2,3]TRIAZOL-4-YL)-PHENOL, DERIVATIVES OF 4-(1-PHENYL-1H-[1,2,3]TRIAZOL-4-YL)-PHENOL, THEIR MEDICAL USE AND THE METHOD OF OBTAINING 4-(1-PHENYL-1H-[1,2,3]TRIAZOL-4-YL)-PHENYL SULFAMATE DERIVATIVES

This Application is a national stage filing under 35 U.S.C. § 371 of International Application No. PCT/PL2018/000080, filed on Aug. 20, 2018, which claims the benefit of PL Application No. P. 425970, filed on Jun. 18, 2018, the contents of which are incorporated herein by reference in their entireties.

The invention relates to 4-(1-phenyl-1H-[1,2,3]triazol-4-yl)-phenyl sulfamate derivatives and derivatives of 4-(1-phenyl-1H-[1,2,3]triazol-4-yl)-phenol as new compounds. The subject of the invention is the first medical use of 4-(1-phenyl-1H-[1,2,3]triazol-4-yl)-phenyl sulfamate derivatives and the first medical use of 4-(1-phenyl-1H-[1,2,3]triazol-4-yl)-phenol analogs. The invention relates to the medical use of 4-(1-phenyl-1H-[1,2,3]triazol-4-yl)-phenyl sulfamate derivatives as pharmaceuticals—for use as medicament—drugs with the action of steroid sulfatase inhibitor and/or with the action of an estrogen receptor modulator as well use of the derivatives as compounds with the properties of a steroid sulfatase inhibitor and/or an estrogen receptor modulator. In addition, the subject of the invention is the medical use of 4-(1-phenyl-1H-[1,2,3]triazol-4-yl)-phenol derivatives as pharmaceuticals—for use as medicament—drugs with the action of an antimicrobial, including antibacterial drugs, and as drugs with the action of an selective estrogen receptor modulator, as well as their use as an antimicrobial and/or an estrogen receptor modulator agents. In particular, the 4-(1-phenyl-1H-[1,2,3]triazol-4-yl)-phenyl sulfamate analogs are for use as medicament in cancer therapy, and in particular in the treatment of hormone-dependent cancers in animals, especially mammals including people. The invention also relates to a process for the preparation of these new compounds, wherein the derivatives of 4-(1-phenyl-1H-[1,2,3]triazol-4-yl)-phenol are the intermediate products to obtaining the sulfamate derivatives.

From document EP1608671, a steroid structure having the general formula

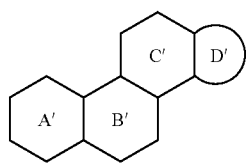

is known. Each of these rings gives the opportunity to replace with a heterocyclic as well as non-heterocyclic rings. It is also known to combine various combinations of a structure imitating a steroid ring with a sulfamate group.

Among the known STS steroid sulfatase inhibitors containing a sulfamate moiety, in particular from EP 1193250, STS inhibitors of the general formula are known:

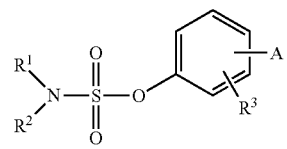

In the publication 1,4-*Diaryl-substituted triazoles as cyclooxygenase-2 inhibitors: Synthesis, biological evaluation and molecular modeling studies*, Kaur J. et al., Bioorganic & Medicinal Chemistry (2013), 21 (14), 4288-4295, chemical compounds containing a sulfonamide group with the formula have been disclosed:

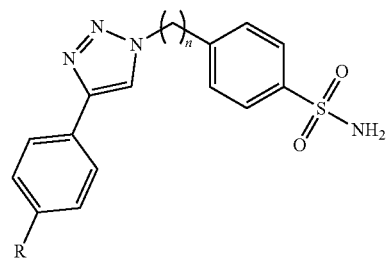

in particular:

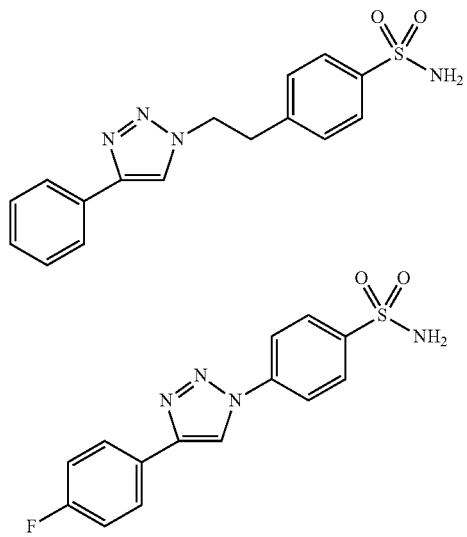

The described compounds exhibited the properties of cyclooxygenase inhibitors.

From WO2015101670, compounds of the general formula are known:

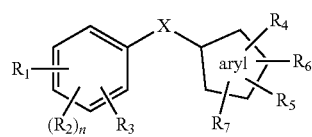

especially:

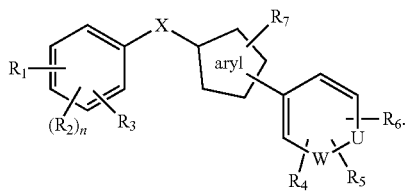

The compounds are useful as 17β-hydroxysteroid dehydrogenase inhibitors. The 17β-hydroxysteroid dehydrogenase enzyme catalyzes the reduction of 17β-steroids including estradiol to estradiol, dehydroepiandrosterone sulfate (DHEAS) to androstendiol sulfate, or dehydroepiandrosterone (DHEA) to androstendiol, and demonstrates the activity in a different pathway of estrogen and androgen biosynthesis in the body compared to the action of steroid sulfatase (STS). Due to the different topology of 17β-hydroxysteroid dehydrogenase and steroid sulfatase active site, inhibition of these enzymes involves compounds that differ structurally and in their mechanism of action.

In the publication *Design, Synthesis, Biological Evaluation and Pharmacokinetics of Bis (hydroxyphenyl) substituted Azoles, Thiophenes, Benzenes, and Aza-Benzenes as Potent and Selective Nonsteroidal Inhibitors of 17β-Hydroxysteroid Dehydrogenase Type 1 (17β-HSD1)*, Bey. E. et al., *J. Med. Chem.*, 2008, 51 (21), pp. 6725-6739, the compounds of the general formula are shown:

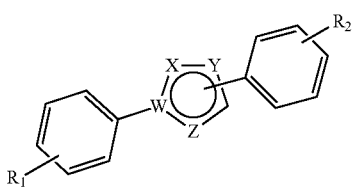

W, X, Y, Z = N, S, Se, C, CH, CCH$_3$
R$_1$, R$_2$ = H, OH

The compounds described have also been used as inhibitors of 17β-hydroxysteroid dehydrogenase. Due to the different topology of 17β-hydroxysteroid dehydrogenase and steroid sulfatase active site, inhibition of these enzymes involves compounds that differ structurally and in their mechanism of action.

The subject of the invention is in particular new chemical compounds defined by the general formula 1:

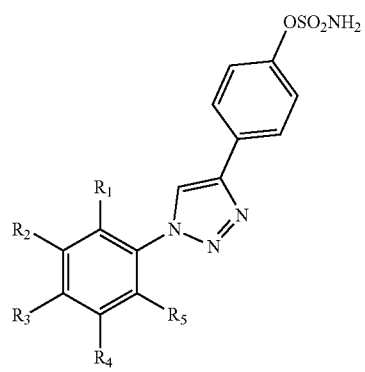

wherein $R_1$ denotes H or F or $CF_3$ or $OCF_3$; $R_2$ denotes H or F or $CF_3$ or Cl or Br or J or $CH_3$ or $OCH_3$ or Et or iPr or $NO_2$; $R_3$ denotes H or F or $CF_3$ or $OCF_3$; $R_4$ denotes H or F or $CF_3$ or Cl or Br or J or $CH_3$ or $OCH_3$; $R_5$ denotes H or F or $CF_3$. The compounds have a structure that mimics the steroid system and contain a sulfamate moiety. Changes with regard to the known steroidal structure according to the invention results in a significant reduction or lack of estrogenic properties of compounds according to the general formula 1, which properties are often a parameter limiting the use of the compounds as a medicament—pharmaceuticals—drugs, in particular with properties of steroid sulfatase inhibitors in oncological clinical practice. These compounds show therefore significant differences compared with known compounds imitating the steroid system, especially in the $R_1$-$R_2$ substituents, which significantly affects the physicochemical properties, the manner and binding efficiency of this compound in the STS active site (as a result of electrostatic interactions) and the strength of enzyme inhibition. The consequence of this is the much higher selectivity of the compounds of the general formula 1 compared to the prior art compounds and the lower or no side effects of these inhibitors, as well as additional unique and important both biological and medical properties—its biological use, diagnostic use and medical use. Exemplary embodiments of the compounds are shown below in Table 1. These compounds have an active medical and biological effect. The compounds therefore are for use as a medicament—in treatment as pharmaceuticals—drugs, and in particular as drugs with a steroid sulfatase inhibitor and/or an estrogen receptor modulator actions, particularly are for use in anti-cancer therapy, especially for therapy of hormone-dependent cancers of animals and especially mammals, including humans. The compounds of the invention have biological and diagnostic applications, including e.g. for use as steroid sulfatase inhibitors and/or estrogen receptor modulators in diagnostics and in vitro tests, and the biological use of the compounds as steroid sulfatase inhibitors and/or estrogen receptor modulators is disclosed.

The invention also relates to novel chemical compounds which are intermediates in the pathway for the preparation of compounds of the general formula 1. These compounds are derivatives of 4-(1-phenyl-1H-[1,2,3]triazol-4-yl)-phenol defined by the general formula 2:

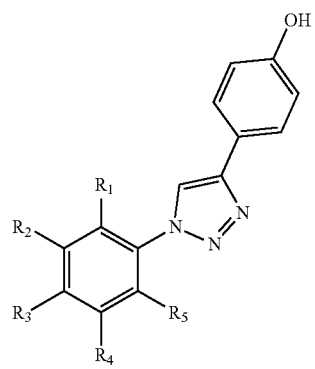

wherein $R_1$ denotes H or F or $CF_3$ or $OCF_3$; $R_2$ denotes H or F or $CF_3$ or Cl or Br or J or $CH_3$ or $OCH_3$ or Et or iPr or $NO_2$; $R_3$ denotes H or F or $CF_3$ or $OCF_3$; $R_4$ denotes H or F or $CF_3$ or Cl or Br or J or $CH_3$ or $OCH_3$; $R_5$ denotes H or F or $CF_3$. The intermediates defined by the general formula 2 and the final products defined by the general formula 1 contain the same important chemical moiety—the scaffold imitating the steroid system while the final product is obtained directly from the intermediate product. The compounds of the general formula 2 have active medical, diagnostic and biological properties, and are for use as a medicament—as pharmaceuticals—drugs, in particular, antimicrobial drugs, including antibacterial drugs or drugs with the action of selective estrogen receptor modulators. The compounds of the general formula 2 show effective antimicrobial activity, including antibacterial effects, exhibit lower toxicity to the body as well as lower ability to induce drug resistance. The compounds of general formula 2 are for use as antimicrobial agent and/or an estrogen receptor modulator properties, especially in diagnostics and in vitro tests and the use of compounds as an antimicrobial compound and/or estrogen receptor modulator is disclosed. The compounds of the general formula 2, due to their structure containing scaffold imitating the steroid system and $R_1$-$R_2$ substituents, affecting the properties of the compounds, especially the binding strength of these compounds to the estrogen receptors, show higher affinity and stronger binding to estrogen receptors in comparison with the compounds disclosed in the prior art and find use in particular as selective estrogen receptor modulators—both in medicine and in general biological sciences. Exemplary preferred compounds of general formula 2 are shown in Table 2. According to preliminary results, these compounds also show antimicrobial activity, especially antibacterial effect.

TABLE 1

Embodiments of 4-(1-phenyl-1H-[1,2,3]triazol-4-yl)-phenyl sulfamate derivatives:

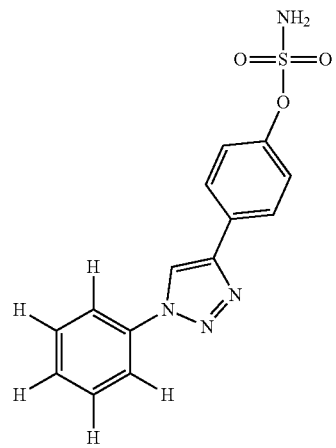

4-(1-phenyl-1H-[1,2,3]triazol-4-yl)-phenyl sulfamate

TABLE 1-continued

Embodiments of 4-(1-phenyl-1H-[1,2,3]triazol-4-yl)-phenyl sulfamate derivatives:

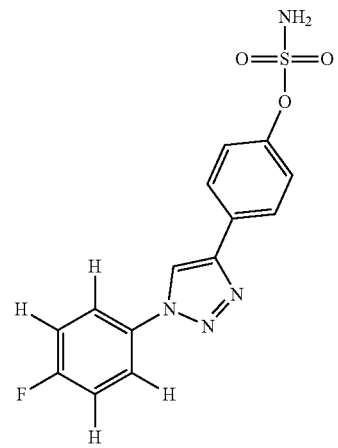

4-[1-(4-fluoro-phenyl)-1H-[1,2,3]triazol-4-yl]-phenyl sulfamate

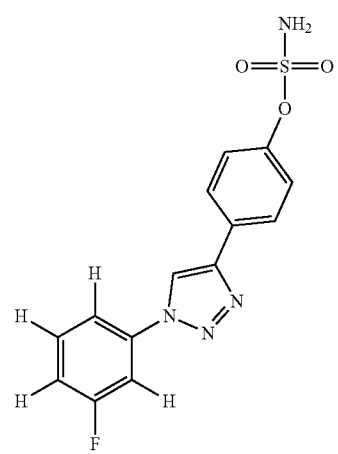

4-[1-(3-fluoro-phenyl)-1H-[1,2,3]triazol-4-yl]-phenyl sulfamate

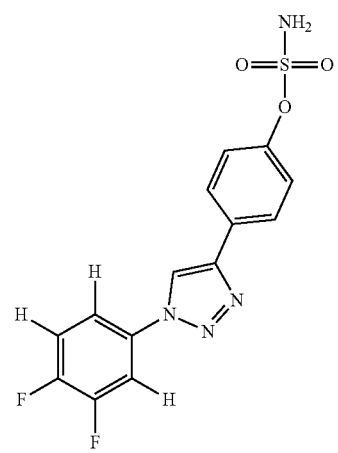

4-[1-(3,4-difluoro-phenyl)-1H-[1,2,3]triazol-4-yl]-phenyl sulfamate

TABLE 1-continued

Embodiments of 4-(1-phenyl-1H-[1,2,3]triazol-4-yl)-phenyl sulfamate derivatives:

4-[1-(3,5-difluoro-phenyl)-1H-[1,2,3]triazol-4-yl]-phenyl sulfamate

4-[1-(2,3,4-trifluoro-phenyl)-1H-[1,2,3]triazol-4-yl]-phenyl sulfamate

4-[1-(4-trifluoromethyl-phenyl)-1H-[1,2,3]triazol-4-yl]-phenyl sulfamate

4-[1-(3-trifluoromethyl-phenyl)-1H-[1,2,3]triazol-4-yl]-phenyl sulfamate

4-[1-(2-trifluoromethyl-phenyl)-1H-[1,2,3]triazol-4-yl]-phenyl sulfamate

TABLE 1-continued
Embodiments of 4-(1-phenyl-1H-[1,2,3]triazol-4-yl)-phenyl sulfamate derivatives:
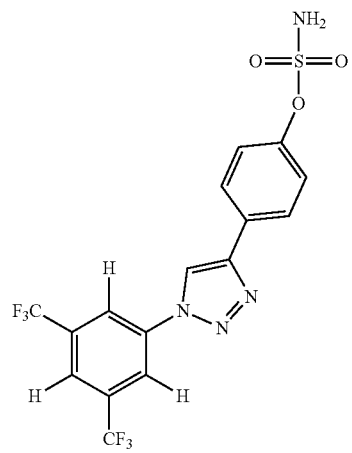
4-[1-(3,5-bis-trifluoromethyl-phenyl)-1H-[1,2,3]triazol-4-yl]-phenyl sulfamate
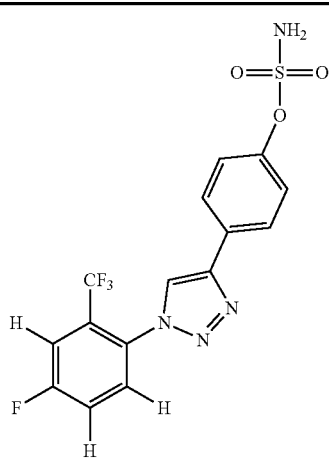
4-[1-(4-fluoro-2-trifluoromethyl-phenyl)-1H-[1,2,3]triazol-4-yl]-phenyl sulfamate
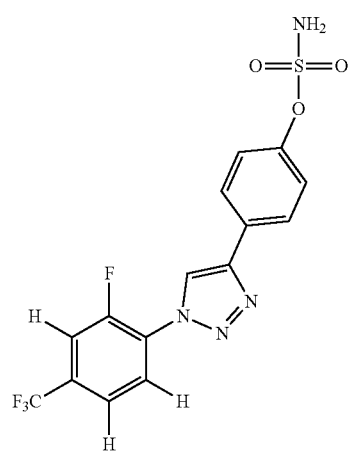
4-[1-(2-fluoro-4-trifluoromethyl-phenyl)-1H-[1,2,3]triazol-4-yl]-phenyl sulfamate
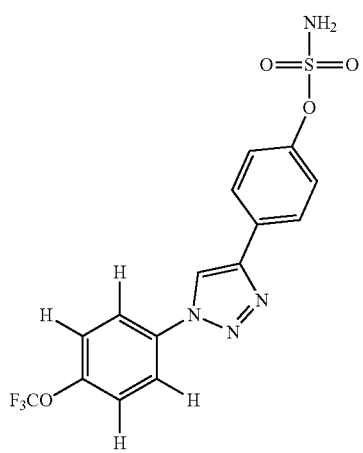
4-[1-(4-trifluoromethoxy-phenyl)-1H-[1,2,3]triazol-4-yl]-phenyl sulfamate TABLE 1-continued
Embodiments of 4-(1-phenyl-1H-[1,2,3]triazol-4-yl)-phenyl sulfamate derivatives:
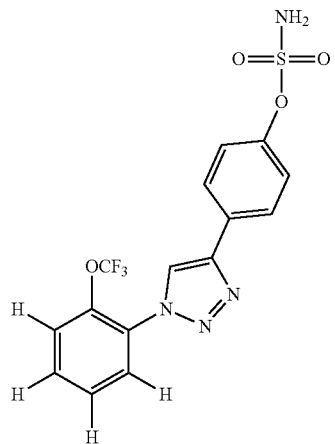
4-[1-(2-trifluoromethoxy-phenyl)-1H-[1,2,3]triazol-4-yl]-phenyl sulfamate
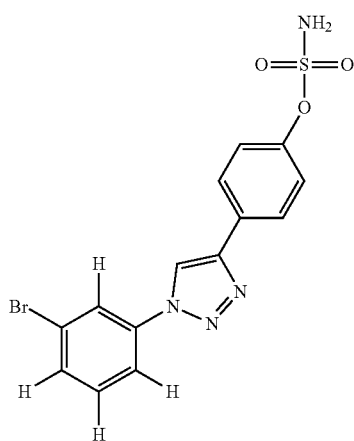
4-[1-(3-bromo-phenyl)-1H-[1,2,3]triazol-4-yl]-phenyl sulfamate
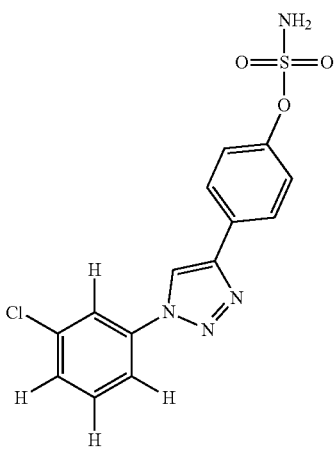
4-[1-(3-chloro-phenyl)-1H-[1,2,3]triazol-4-yl]-phenyl sulfamate
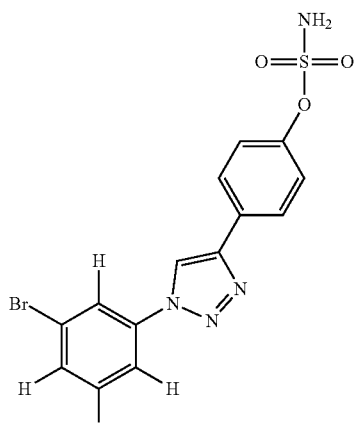
4-[1-(3,5-dibromo-phenyl)-1H-[1,2,3]triazol-4-yl]-phenyl sulfmate
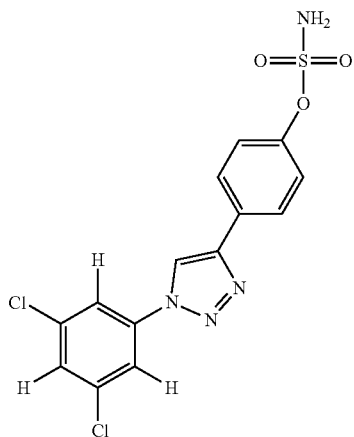
4-[1-(3,5-dichloro-phenyl)-1H-[1,2,3]triazol-4-yl]-phenyl sulfamate
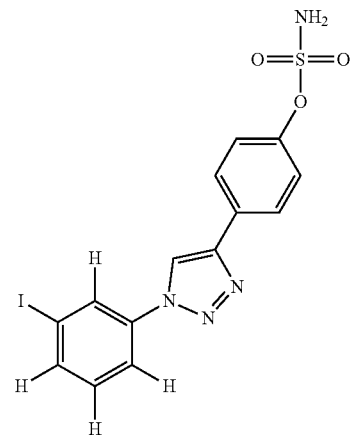
4-[1-(3-iodo-phenyl)-1H-[1,2,3]triazol-4-yl]-phenyl sulfmate TABLE 1-continued
Embodiments of 4-(1-phenyl-1H-[1,2,3]triazol-4-yl)-phenyl sulfamate derivatives:
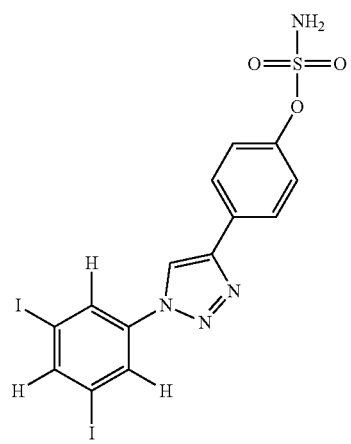
4-[1-(3,5-diiodo-phenyl)-1H-[1,2,3]triazol-4-yl]-phenyl sulfamate
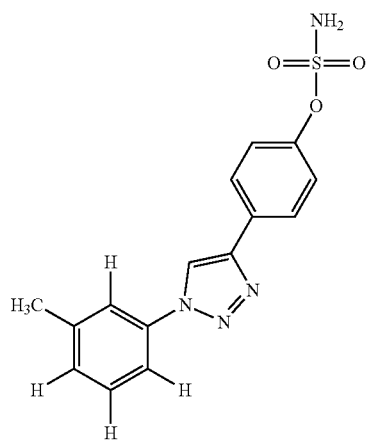
4-(1-m-tolyl-1H-[1,2,3]triazol-4-yl)-phenyl sulfamate
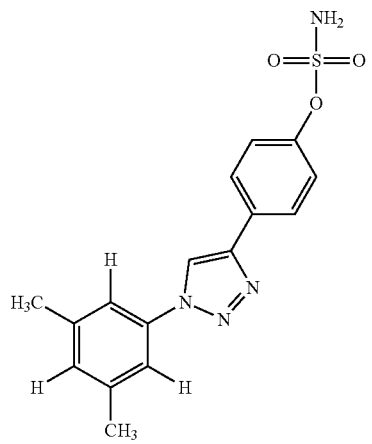
4-[1-(3,5-dimethyl-phenyl)-1H-[1,2,3]triazol-4-yl]-phenyl sulfamate
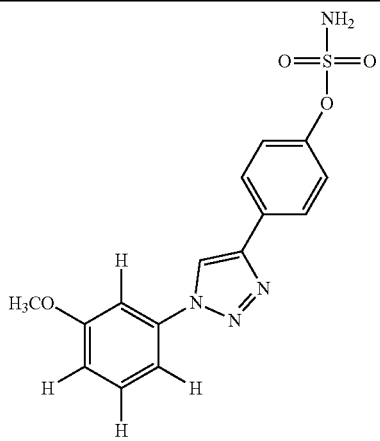
4-[1-(3-methoxy-phenyl)-1H-[1,2,3]triazol-4-yl]-phenyl sulfamate
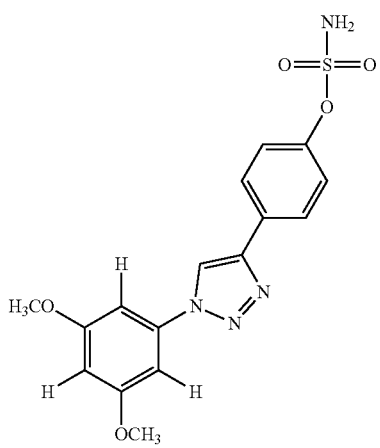
4-[1-(3,5-dimethoxy-phenyl)-1H-[1,2,3]triazol-4-yl]-phenyl sulfamate
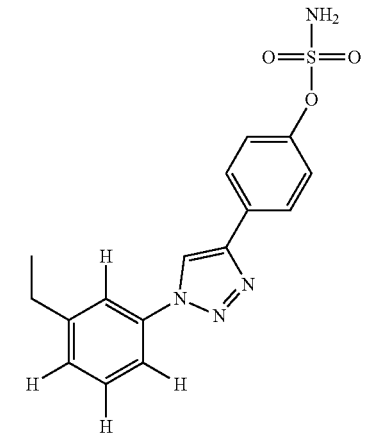
4-[1-(3-ethyl-phenyl)-1H-[1,2,3]triazol-4-yl]-phenyl sulfamate TABLE 1-continued
Embodiments of 4-(1-phenyl-1H-[1,2,3]triazol-4-yl)-phenyl sulfamate derivatives:
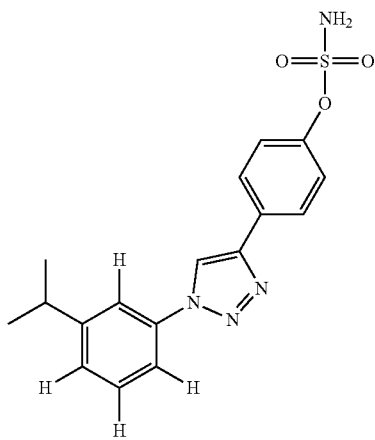
4-[1-(3-isopropyl-phenyl)-1H-[1,2,3]triazol-4-yl]-phenyl sulfamate
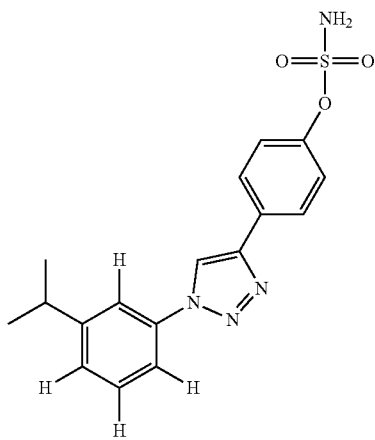
4-[1-(3-nitro-phenyl)-1H-[1,2,3]triazol-4-yl]-phenyl sulfamate
TABLE 2
Embodiment of derivatives of 4-(1-phenyl-1H-[1,2,3]triazol-4-yl)-phenol:
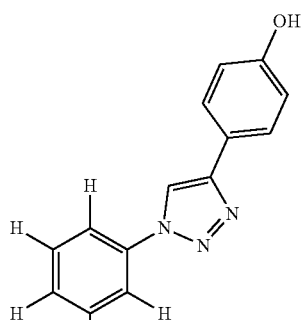
4-(1-phenyl-1H-[1,2,3]triazol-4-yl)-phenol
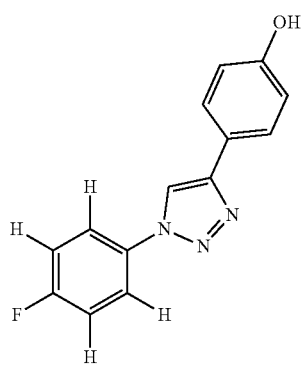
4-[1-(4-fluoro-phenyl)-1H-[1,2,3]triazol-4-yl]-phenol
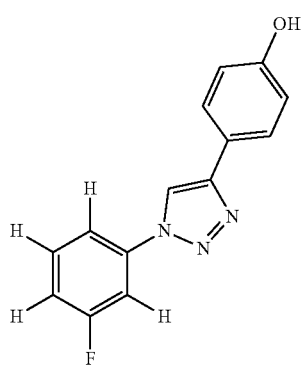
4-[1-(3-fluoro-phenyl)-1H-[1,2,3]triazol-4-yl]-phenol TABLE 2-continued Embodiment of derivatives of 4-(1-phenyl-1H-[1,2,3]triazol-4-yl)-phenol:

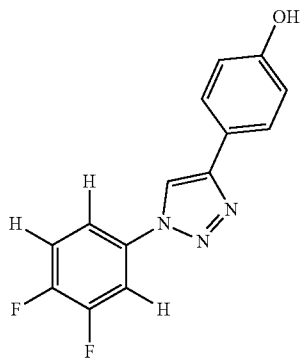

4-[1-(3,4-difluoro-phenyl)-1H-[1,2,3]triazol-4-yl]-phenol

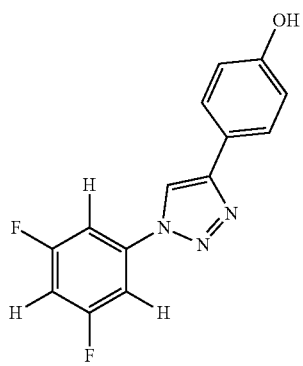

4-[1-(3,5-difluoro-phenyl)-1H-[1,2,3]triazol-4-yl]-phenol

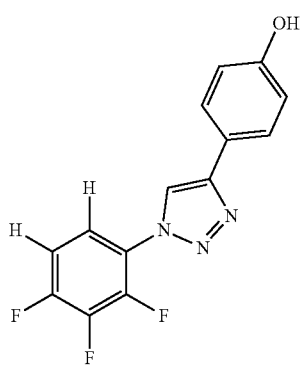

4-[1-(2,3,4-trifluoro-phenyl)-1H-[1,2,3]triazol-4-yl]-phenol

TABLE 2-continued

Embodiment of derivatives of 4-(1-phenyl-1H-[1,2,3]triazol-4-yl)-phenol:

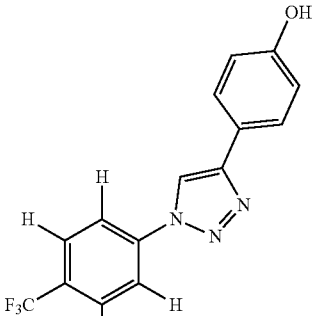

4-[1-(4-trifluoromethyl-phenyl)-1H-[1,2,3]triazol-4-yl]-phenol

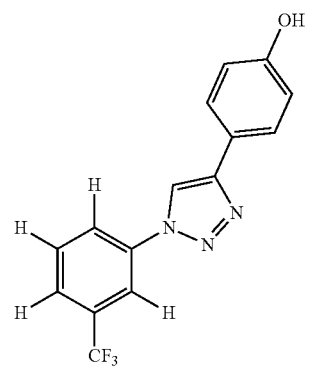

4-[1-(3-trifluoromethyl-phenyl)-1H-[1,2,3]triazol-4-yl]-phenol

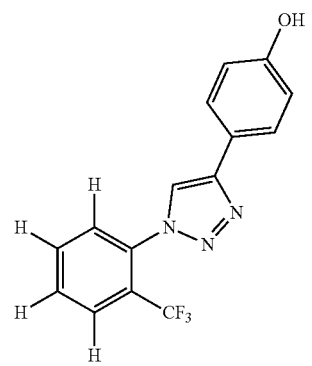

4-[1-(2-trifluoromethyl-phenyl)-1H-[1,2,3]triazol-4-yl]-phenol

TABLE 2-continued

Embodiment of derivatives of 4-(1-phenyl-1H-[1,2,3]triazol-4-yl)-phenol:

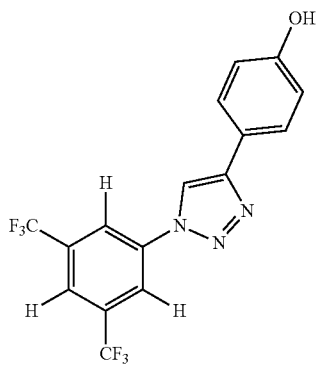 [SMILES: Oc1ccc(-c2cn(-c3cc(C(F)(F)F)cc(C(F)(F)F)c3)nn2)cc1]

4-[1-(3,5-bis-trifluoromethyl-phenyl)-1H-[1,2,3]triazol-4-yl]-phenol

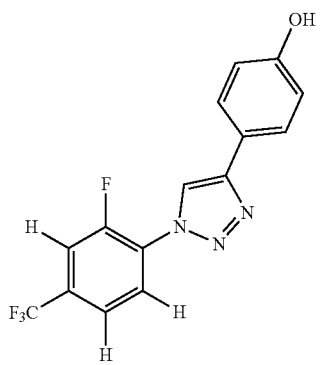

4-[1-(2-fluoro-4-trifluoromethyl-phenyl)-1H-[1,2,3]triazol-4-yl]-phenol

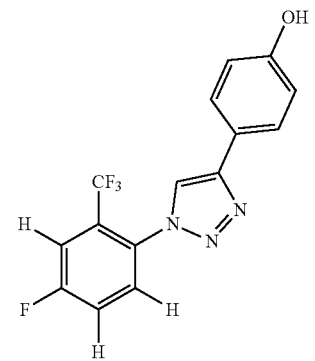

4-[1-(4-fluoro-2-trifluoromethyl-phenyl)-1H-[1,2,3]triazol-4-yl]-phenol

TABLE 2-continued

Embodiment of derivatives of 4-(1-phenyl-1H-[1,2,3]triazol-4-yl)-phenol:

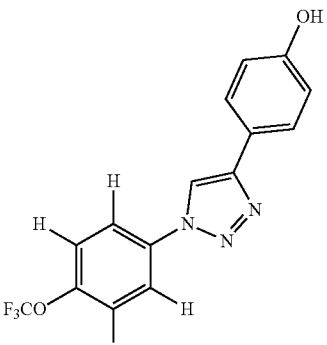

4-[1-(4-trifluoromethoxy-phenyl)-1H-[1,2,3]triazol-4-yl]-phenol

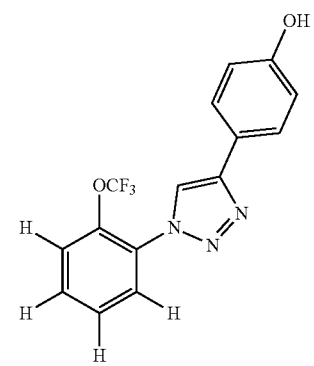

4-[1-(2-trifluoromethoxy-fenylo)-1H-[1,2,3]triazol-4-yl]-phenol

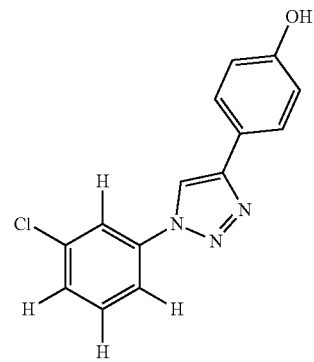

4-[1-(3-chloro-phenyl)-1H-[1,2,3]triazol-4-yl]-phenol

TABLE 2-continued
Embodiment of derivatives of 4-(1-phenyl-1H-[1,2,3]triazol-4-yl)-phenol:
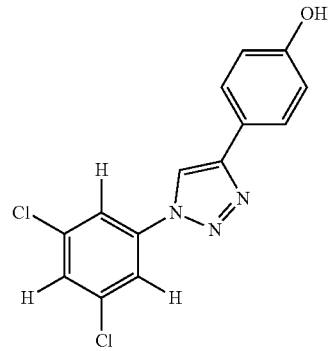
4-[1-(3,5-dichloro-phenyl)-1H-[1,2,3]triazol-4-yl]-phenol
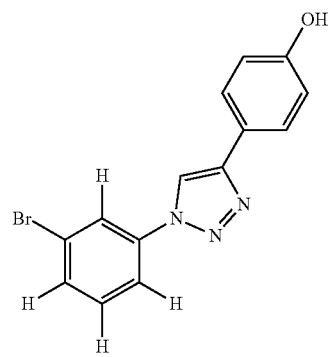
4-[1-(3-bromo-phenyl)-1H-[1,2,3]triazol-4-yl]-phenol
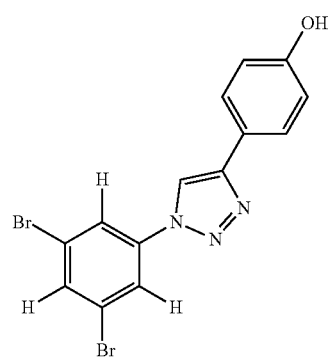
4-[1-(3,5-dibromo-phenyl)-1H-[1,2,3]triazol-4-yl]-phenol
TABLE 2-continued
Embodiment of derivatives of 4-(1-phenyl-1H-[1,2,3]triazol-4-yl)-phenol:
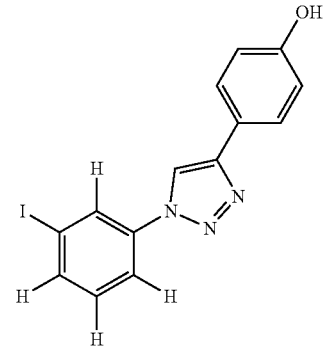
4-[1-(3-iodo-phenyl)-1H-[1,2,3]triazol-4-yl]-phenol
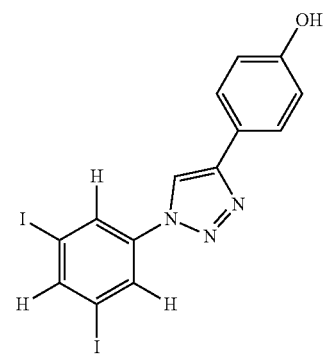
4-[1-(3,5-diiodo-phenyl)-1H-[1,2,3]triazol-4-yl]-phenol
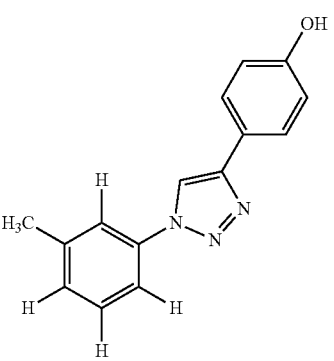
4-(1-m-tolyl-1H-[1,2,3]triazol-4-yl)-phenol TABLE 2-continued
Embodiment of derivatives of 4-(1-phenyl-1H-[1,2,3]triazol-4-yl)-phenol:
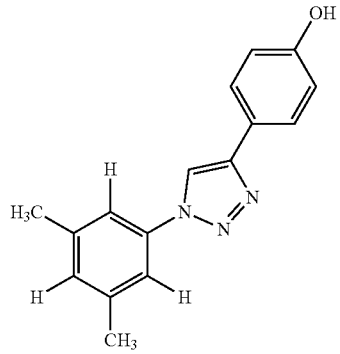
4-[1-(3,5-dimethyl-phenyl)-
1H-[1,2,3]triazol-4-yl]-
phenol
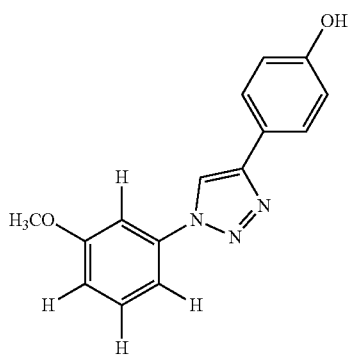
4-[1-(3-methoxy-phenyl)-
1H-[1,2,3]triazol-4-yl]-phenol
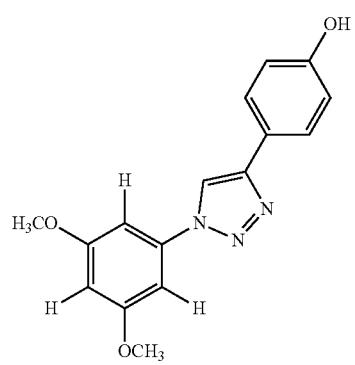
4-[1-(3,5-dimethoxy-phenyl)-
1H-[1,2,3]triazol-4-yl]-phenol
TABLE 2-continued
Embodiment of derivatives of 4-(1-phenyl-1H-[1,2,3]triazol-4-yl)-phenol:
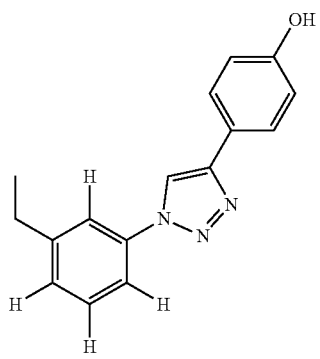
4-[1-(3-ethyl-phenyl)-
1H-[1,2,3]triazol-4-yl]-phenol
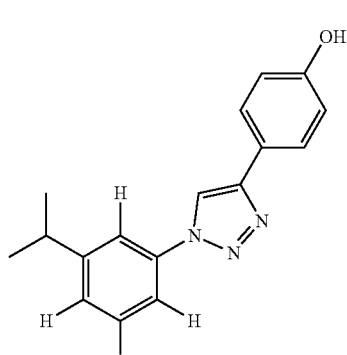
4-[1-(3-isopropyl-
phenyl)-1H-[1,2,3]triazol-
4-yl]-phenol
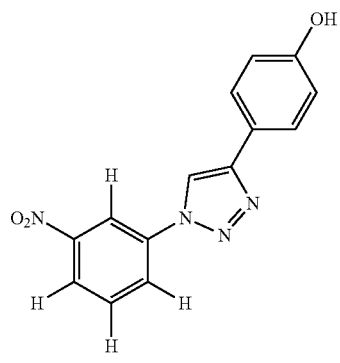
4-[1-(3-nitro-phenyl)-1H-
[1,2,3]triazol-4-yl]-phenol The subject of the invention is also a method for the preparation of compound defined by the general formula 1:
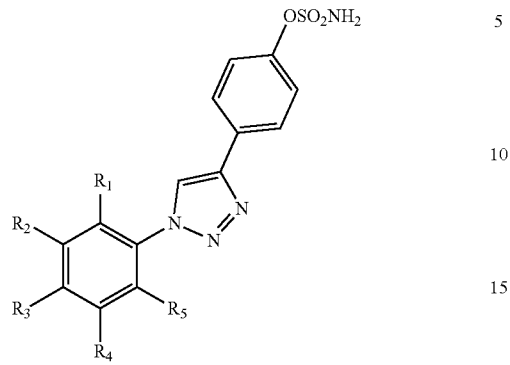
wherein $R_1$=H, F, $CF_3$, $OCF_3$; $R_2$=H, F, $CF_3$, Cl, Br, J, $CH_3$, $OCH_3$, Et, iPr, $NO_2$; $R_3$=H, F, $CF_3$, $OCF_3$; $R_4$=H, F, $CF_3$, Cl, Br, J, $CH_3$, $OCH_3$; $R_5$=H, F, $CF_3$,
wherein the method is carried out in several steps according to scheme 1:
Scheme 1
Step 1
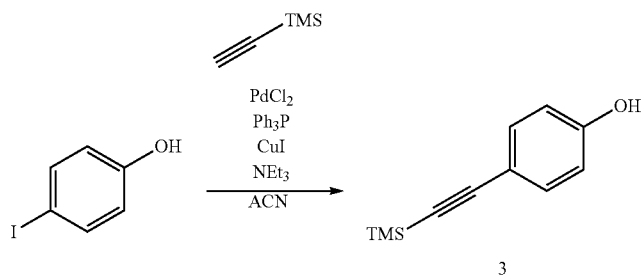
Step 2
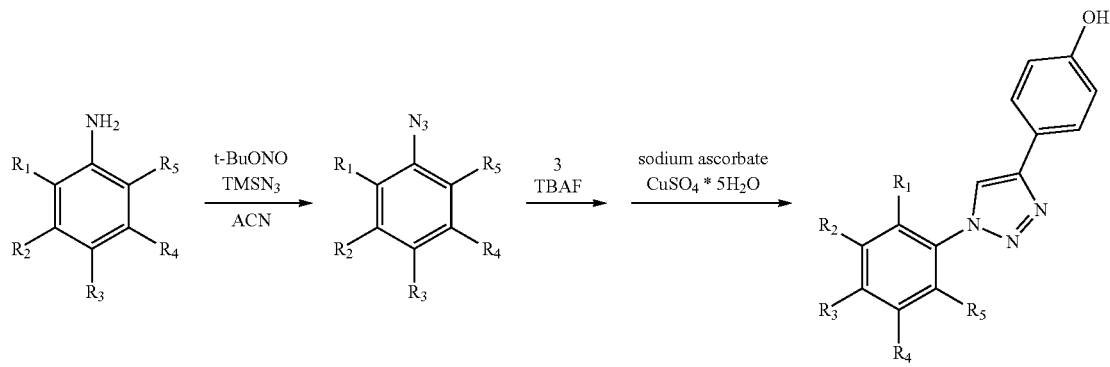
Step 3
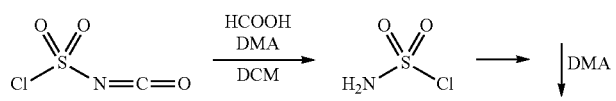

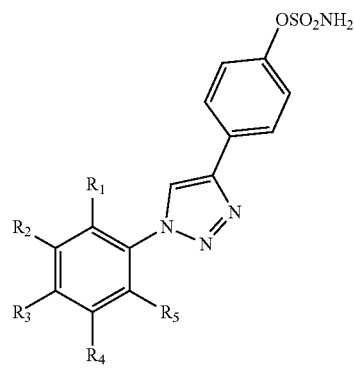

In the first step, 4-((trimethylsilyl)ethynyl)phenol (3) is obtained from p-iodophenol and trimethylsilylacetylene by the Sonogashira coupling reaction and this step is carried out under reflux. In the second step, derivatives of 4-(1-phenyl-1H-[1,2,3]triazol-4-yl)-phenol (4) are obtained by the reaction of 1,3-dipolar cycloaddition of corresponding azide derivative with 4-((trimethylsilyl)ethynyl)phenol (3), preferably in the presence of tetrabutylammonium fluoride (TBAF) or with 4-ethynylphenol. In the third step, the final product is obtained by reaction of sulfamoyl chloride (generated in situ) with the 4-(1-phenyl-1H-[1,2,3]triazol-4-yl)-phenol derivative (4) and this step is carried out under anhydrous conditions.

Preferably, the first step is carried out over a minimum of 1 hour, preferably over 2 to 24 hours.

Preferably, the second step is carried out at room temperature.

Preferably, the second step is carried out in situ without isolation or with isolation.

Preferably, the second step is carried out over at least 12 hours, preferably over 12 to 48 hours.

Preferably, the third step is carried out under anhydrous conditions at a temperature in the range of 15 to 40° C., preferably 30-40° C., preferably at room temperature.

Preferably, the third step is carried out over a minimum of 6 hours.

EXAMPLES

A) Preparation of Compounds of General Formula 1:

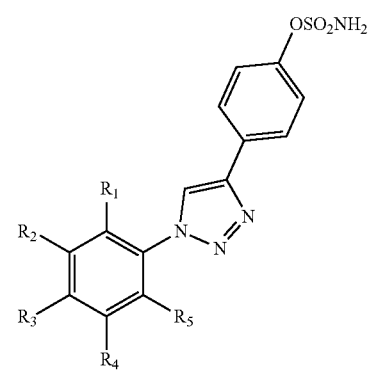

wherein $R_1$=H or F or $CF_3$ or $OCF_3$; $R_2$=H or F or $CF_3$ or Cl or Br or J or $CH_3$ or $OCH_3$ or Et or iPr or $NO_2$; $R_3$=H or F or $CF_3$ or $OCF_3$; $R_4$=H or F or $CF_3$ or Cl or Br or J or $CH_3$ or $OCH_3$; $R_5$=H or F or $CF_3$, was carried out according to the method shown in scheme 1:

Scheme 1

Step 1

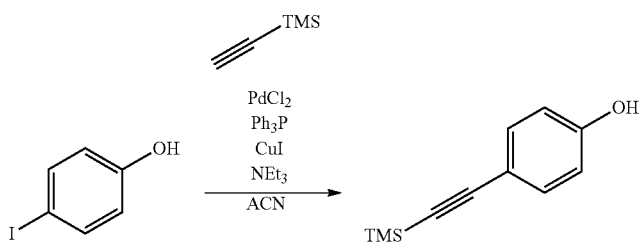

Step 2

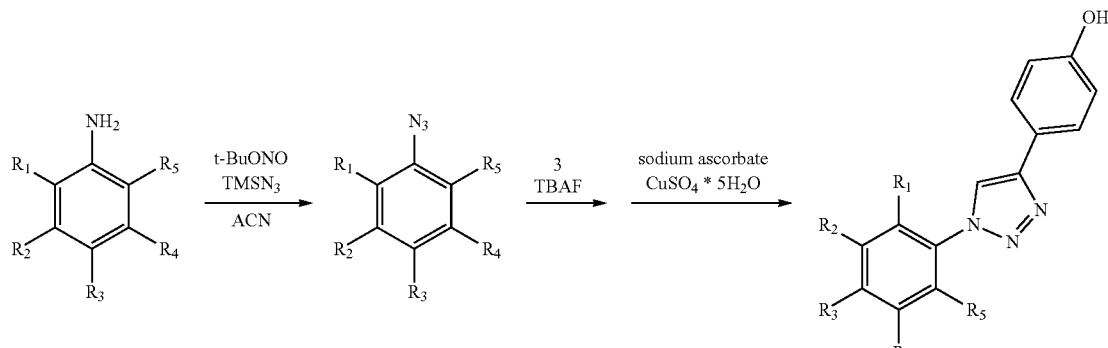

Step 3

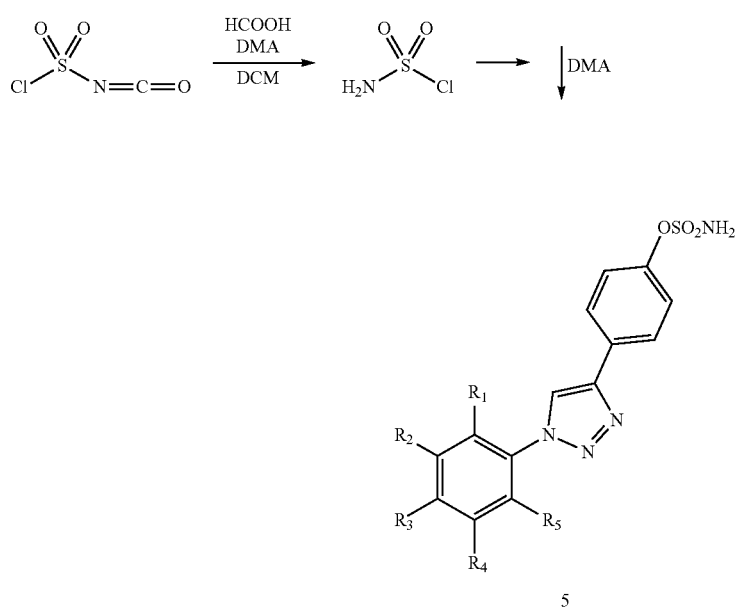

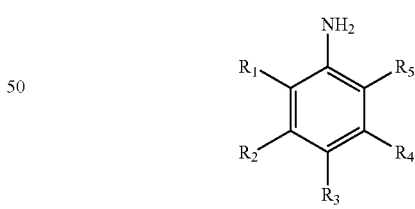

Synthesis of new steroid sulfatase (STS) inhibitors basd on 4-(1-phenyl-1H-[1,2,3]triazol-4-yl)-phenyl sulfamate derivatives (5);
ACN—acetonitrile, TMS—trimethylsilane, tBuONO—tertbutylnitrite, TMSN₃—trimethylsilyl azide, TBAF—tetrabutylammonium fluride, N,N′-DMA—dimethylacetamide, DCM—dichloromethane.

The first step includes the preparation of 4-((trimethylsilyl)ethynyl)phenol (3) by the Sonogashira coupling reaction of p-iodophenol and trimethylsilylacetylene. The second step involves the synthesis of 4-(1-phenyl-1H-[1,2,3]triazol-4-yl)-phenol derivatives (4) as a result of the 1,3-dipolar cycloaddition reaction of the azide derivative with 4-((trimethylsilyl)ethynyl)phenol (3) in the presence of tetrabutylammonium fluoride (TBAF)/or with 4-ethynyl phenol in situ without isolation/or with isolation of intermediates. In the second step, intermediates of general formula 2 are obtained. The third step involves obtaining the final product as a result of the reaction of sulfamoyl chloride (generated in situ) with the 4-(1-phenyl-1H-[1,2,3]triazol-4-yl)-phenol derivative (4).

Depending on the final product to be synthesized, a various substrate is used to the reaction, i.e. the aniline derivative of the general formula 3 substituted in the aromatic ring:

wherein $R_1$=H or F or $CF_3$ or $OCF_3$; $R_2$=H or F or $CF_3$ or Cl or Br or J or $CH_3$ or $OCH_3$ or Et or iPr or $NO_2$; $R_3$=H or F or $CF_3$ or $OCF_3$; $R_4$=H or F or $CF_3$ or Cl or Br or J or $CH_3$ or $OCH_3$; $R_5$=H or F or $CF_3$.

The substituents in the substrate are selected for the intermediates and the final product, as is known to a person skilled in the art. The corresponding synthesis steps, for variants of the invention, are shown below.

Step 1:

Preparation of 4-((trimethylsilyl)ethynyl)phenol (3)

A solution of 4-iodophenol (0.88 g, 4 mmol), trimethylsilylacetylene (0.855 mL, 6 mmol), palladium (II) chloride (35.8 mg, 0.20 mmol), triphenylphosphine (0.106 g, 0.40 mmol), copper (I) iodide (19 mg, 0.10 mmol) and triethylamine (3.94 mL, 28.2 mmol) in acetonitrile (20 mL) was prepared in a round bottom flask. The reaction mixture was heated under reflux for 3 hours in an inert gas atmosphere. After this time, the reaction mixture was filtered and the solvent was evaporated. The product of 4-((trimethylsilyl)ethynyl)phenol (3) was isolated using preparative column chromatography (in the normal phase) using a mixture of ethyl acetate and hexane in a 1:4 volume ratio as an eluent.

Yield 70%; melting point 63-66° C.; $v_{max}$ (KBr)/cm$^{-1}$ 3308, 2956, 2160, 1606, 1508, 1434, 1356, 1206, 826; $^1$H NMR $\delta_H$ (400 MHz, CDCl$_3$) 7.38 (2H, d, J 8.8 Hz, Ar—H), 6.77 (2H, d, J 8.8, Ar—H), 6.00-3.40 (1H, brs, OH), 0.26 (9H, s, CH$_3$); $^{13}$C NMR $\delta_C$ (101 MHz, CDCl$_3$) 155.8, 133.7, 115.5, 115.4, 105.1, 92.6, 0.1. HRMS (m/z) [M−H]− calculated 189.0741, observed 189.0951.

Step 2:

General Procedure for the Preparation of 4-(1-phenyl-1H-[1,2,3]triazol-4-yl)-phenol Derivatives (4)

To a cooled solution of the appropriate amine (2.63 mmol) in acetonitrile (6.1 mL), tert-butyl nitrite (0.325 g, 3.16 mmol) and azidotrimethylsilane (0.333 g, 2.89 mmol) were added dropwise. After stirring at room temperature for 4 hours, 4-((trimethylsilyl)ethynyl)phenol (3) (0.5 g, 2.63 mmol) and a 1 M solution of tetrabutylammonium fluoride in THF (2.89 mL) were added. The mixture was stirred at 0° C. for 30 min. Then a freshly prepared solution of sodium ascorbate (0.104 g, 0.526 mmol) in 0.525 mL of water and copper (II) sulfate pentahydrate (65.7 mg, 0.263 mmol) were added to the reaction mixture. The mixture was stirred for 24 hours under an inert gas atmosphere. The reaction mixture was then evaporated under reduced pressure and the residue was dissolved in ethyl acetate (30 mL). The solution was washed with 0.1 M HCl. The separated organic layer was dried over anhydrous magnesium sulfate, filtered and the solvent was evaporated under reduced pressure. The obtained crude product was crystallized from acetonitrile.

Example 1

Step 2

Preparation of 4-[1-(3,5-Bis-trifluoromethyl-phenyl)-1H-[1,2,3]triazol-4-yl]-phenol

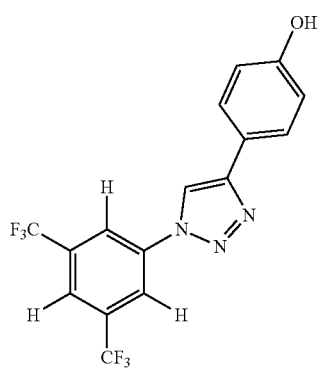

To an ice-cooled solution of 3,5-bis-(trifluoromethyl)aniline (0.603 g, 2.63 mmol) in acetonitrile (6.1 mL), tert-butyl nitrite (0.325 g, 3.16 mmol) and azidotrimethylsilane (0.333 g, 2.89 mmol) were added dropwise. After stirring at room temperature for 4 hours, 4-((trimethylsilyl)ethynyl)phenol (3) (0.5 g, 2.63 mmol) and a 1 M solution of tetrabutylammonium fluoride in THF (2.89 mL) were added. The mixture was stirred at 0° C. for 30 min. Then a freshly prepared solution of sodium ascorbate (0.104 g, 0.526 mmol) in 0.525 mL of water and copper (II) sulfate pentahydrate (65.7 mg, 0.263 mmol) were added to the reaction mixture. The mixture was stirred for 24 hours under an inert gas atmosphere. The reaction mixture was then evaporated under reduced pressure and the residue was dissolved in ethyl acetate (30 mL). The solution was washed with 0.1 M HCl. The separated organic layer was dried over anhydrous magnesium sulfate, filtered and the solvent was evaporated under reduced pressure. The obtained crude product was crystallized from acetonitrile.

Yield 66%; melting point 270-272° C.; $v_{max}$ (KBr)/cm$^{-1}$ 3172, 1615, 1492, 1426, 1361, 1223, 1054, 846; $^1$H NMR $\delta_H$ (400 MHz, DMSO) 9.72 (1H, s, OH), 9.43 (1H, s, CH), 8.65 (2H, s, Ar—H), 8.26 (1H, s, Ar—H), 7.75 (2H, d, J 8.6 Hz, Ar—H), 6.90 (2H, d, J 8.7 Hz, Ar—H); $^{13}$C NMR $\delta_C$ (101 MHz, DMSO) 158.3, 148.6, 138.4, 132.3 (m), 127.3, 123.3 (q, $^1J_{C-F}$ 273 Hz), 122.2 (m), 121.1, 120.8 (m), 119.1, 116.3. HRMS (m/z) [M+H]+ calculated 374.0728, observed 374.0757.

Example 2

Step 2

Preparation of 4-[1-(3,5-difluoro-phenyl)-1H-[1,2,3]-triazol-4-yl]-phenol

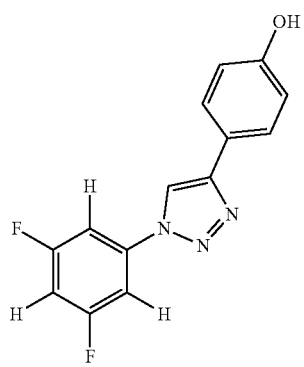

To an ice-cooled solution of 3,5-difluoroaniline (0.340 g, 2.63 mmol) in acetonitrile (6.1 mL), tert-butyl nitrite (0.325 g, 3.16 mmol) and azidotrimethylsilane (0.333 g, 2.89 mmol) were added dropwise. After stirring at room temperature for 4 hours, 4-((trimethylsilyl)ethynyl)phenol (3) (0.5 g, 2.63 mmol) and a 1 M solution of tetrabutylammonium fluoride in THF (2.89 mL) were added. The mixture was stirred at 0° C. for 30 min. Then a freshly prepared solution of sodium ascorbate (0.104 g, 0.526 mmol) in 0.525 mL of water and copper (II) sulfate pentahydrate (65.7 mg, 0.263 mmol) were added to the reaction mixture. The mixture was stirred for 24 hours under an inert gas atmosphere. The reaction mixture was then evaporated under reduced pressure and the residue was dissolved in ethyl acetate (30 mL). The solution was washed with 0.1 M HCl. The separated organic layer was dried over anhydrous magnesium sulfate, filtered and the solvent was evaporated under reduced pressure. The obtained crude product was crystallized from acetonitrile.

Yield 63%; melting point 214-216° C.; $v_{max}$ (KBr)/cm$^{-1}$ 3333, 1627, 1493, 1408, 1331, 1216, 1029, 823; $^1$H NMR $\delta_H$ (400 MHz, DMSO) 9.71 (1H, s, OH), 9.19 (1H, s, CH), 7.85-7.67 (4H, m, Ar—H), 7.47-7.35 (1H, m, Ar—H), 6.90 (2H, d, J 8.7 Hz, Ar—H); $^{13}$C NMR $\delta_C$ (101 MHz, DMSO) 163.4 (d, $^1J_{C-F}$ 247 Hz),158.3, 148.4, 138.9 (m), 127.3, 121.2, 118.8, 116.3, 104.3 (m), 104.1 (m). HRMS (m/z) [M+H]+ calculated 274.0792, observed 274.0812.

Step 3:

General Procedure for the Preparation of 4-(1-phenyl-1H-[1,2,3]triazol-4-yl)-phenyl Sulfamate Derivatives (5)

To a solution of chlorosulfonyl isocyanate (212.3 mg, 1.50 mmol) in anhydrous dichloromethane (0.5 mL) was added a mixture of formic acid (70.9 mg, 1.54 mmol) and N,N-dimethylacetamide (1.4 mg, 0.016 mmol). The mixture was stirred at 40° C. for 3.5 hours. A solution of 4-(1-phenyl-1H-[1,2,3]triazol-4-yl)-phenol (4) (1.00 mmol) in N,N-dimethylacetamide (3.4 mL) was then added to the reaction mixture. The mixture was stirred for 24 hours at room temperature. After this time, the reaction mixture was poured into water (50 mL). The resulting suspension was stirred for 2 hours. The precipitated crude product was filtered, washed with water and crystallized from acetonitrile.

Example 1

Step 3

Preparation of 4-[1-(3,5-Bis-trifluoromethyl-phenyl)-1H-[1,2,3]triazol-4-yl]-phenyl sulfamate

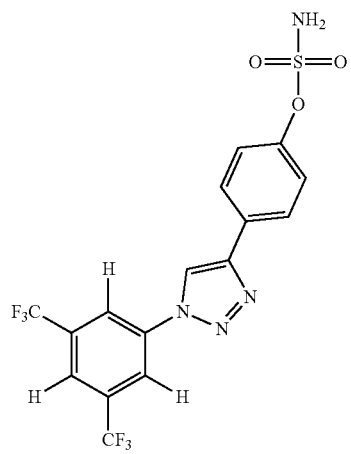 [SMILES: NS(=O)(=O)Oc1ccc(-c2cn(-c3cc(C(F)(F)F)cc(C(F)(F)F)c3)nn2)cc1]

To a solution of chlorosulfonyl isocyanate (212.3 mg, 1.50 mmol) in anhydrous dichloromethane (0.5 mL) was added a mixture of formic acid (70.9 mg, 1.54 mmol) and N,N-dimethylacetamide (1.4 mg, 0.016 mmol). The mixture was stirred at 40° C. for 3.5 hours. Then a solution of 4-[1-(3,5-Bis-trifluoromethyl-phenyl)-1H-[1,2,3]triazol-4-yl]-phenol (0.373 g, 1.00 mmol) (obtained according to the procedure shown in example 1, step 2) in N,N-dimethylacetamide (3.4 mL) was added to the reaction mixture. The mixture was stirred for 24 hours at room temperature. After this time, the reaction mixture was poured into water (50 mL). The resulting suspension was stirred for 2 hours. The precipitated crude product was filtered, washed with water and crystallized from acetonitrile.

Yield 79%; melting point 231-232° C.; $v_{max}$ (KBr)/cm$^{-1}$ 3358, 3145, 1493, 1373, 1277, 1153, 1052, 808, 755; $^1$H NMR $\delta_H$ (400 MHz, DMSO) 9.65 (1H, s, CH), 8.68 (2H, s, Ar—H), 8.30 (1H, s, Ar—H), 8.10 (2H, s, NH$_2$), 8.02 (2H, d, J 8.7 Hz, Ar—H), 7.45 (2H, d, J 7.45 Hz, Ar—H); $^{13}$C NMR $\delta_C$ (101 MHz, DMSO) 150.6, 147.6, 138.3, 132.4 (m), 128.6, 127.2, 123.4, 123.3 (q, $^1J_{C-F}$ 273 Hz), 122.6 (m), 121.1 (m), 121.0. HRMS (m/z) [M+H]+ calculated 453.0456, observed 453.0511.

Example 2

Step 3

Preparation of 4-[1-(3,5-difluoro-phenyl)-1H-[1,2,3]-triazol-4-yl]-phenyl sulfamate

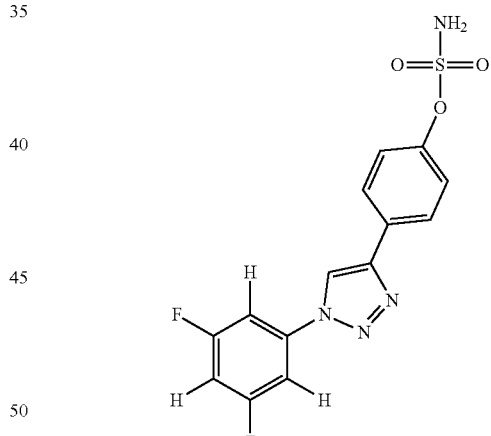

To a solution of chlorosulfonyl isocyanate (212.3 mg, 1.50 mmol) in anhydrous dichloromethane (0.5 mL) was added a mixture of formic acid (70.9 mg, 1.54 mmol) and N,N-dimethylacetamide (1.4 mg, 0.016 mmol). The mixture was stirred at 40° C. for 3.5 hours. Then a solution of 4-[1-(3,5-difluoro-phenyl)-1H-[1,2,3]-triazol-4-yl]-phenol (0.273 g, 1.00 mmol) (obtained according to the procedure shown in example 2, step 2) in N,N-dimethylacetamide (3.4 mL) was added to the reaction mixture. The mixture was stirred for 24 hours at room temperature. After this time, the reaction mixture was poured into water (50 mL). The resulting suspension was stirred for 2 hours. The precipitated crude product was filtered, washed with water and crystallized from acetonitrile.

Yield 80%; melting point 227-228° C.; $v_{max}$ (KBr)/cm$^{-1}$ 3343, 3155, 1493, 1376, 1227, 1157, 1056, 844, 756; $^1$H NMR $\delta_H$ (400 MHz, DMSO) 9.42 (1H, s, CH), 8.09 (1H, s, NH$_2$), 7.99 (2H, d, J 8.7 Hz, Ar—H), 7.86-7.76 (2H, m, Ar—H), 7.51-7.40 (3H, m, Ar—H); $^{13}$C NMR $\delta_C$ (101 MHz, DMSO) 163.4 (d, $^1J_{C-F}$ 247 Hz), 150.6, 147.2, 138.8 (m), 128.7, 127.2, 123.4, 120.6, 104.5 (m), 104.3 (m). HRMS (m/z) [M+H]+ calculated 353.0520, observed 353.0548.

In a similar manner, the other compounds of general formula 1 and 2 are obtained.

B) Biological and Medical Evaluation of the Obtained Derivatives in the Enzymatic Assay—Study of the Properties of the Compounds for Use as a Medicament and for Use as a Diagnostic Agents as Well as its Biological Use.

Studies on in vitro activity of the new compounds presented by the general formula 1:

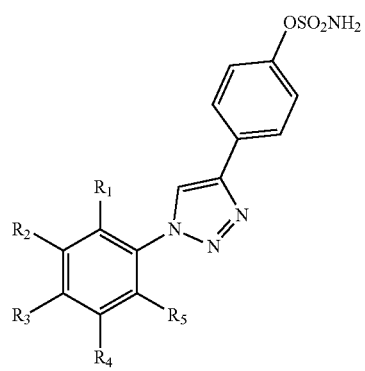

wherein R$_1$=H or F or CF$_3$ or OCF$_3$; R$_2$=H or F or CF$_3$ or Cl or Br or J or CH$_3$ or OCH$_3$ or Et or iPr or NO$_2$; R$_3$=H or F or CF$_3$ or OCF$_3$; R$_4$=H or F or CF$_3$ or Cl or Br or J or CH$_3$ or OCH$_3$; R$_5$=H or F or CF$_3$.

The medical and biological activity of the compounds defined the general formula 1, for use as active compounds—medicament—drugs and/or as STS steroid sulfatase inhibitors, diagnostic agent and biological use were evaluated using the STS steroid sulfatase enzyme isolated from a human placenta according to the following procedure:

human placenta was stripped from membranes and homogenized in ice-cold Tris-HCl buffer pH 7.4 containing 0.1% Triton X-100 and 0.02% NaN$_3$.

the homogenate was alternately frozen and thawed a few times and then centrifuged at 100000 g for 60 min, the supernatant was removed and the same procedure from homogenization to centrifugation was carried out 5 times, finally, the enzyme was purified by three-step chromatography using columns: DEAE-cellulose, Con A-Sepharose and Bio-Gel A-1.5 and appropriate buffers. All steps were carried out at 4° C.

The biological, diagnostics and medical activity of STS inhibitors, for the compounds defined by the general formula 1, were evaluated by analyzing the progress of the enzymatic reaction using nitrophenyl sulfate (NPS). The final volume of the reaction mixture was 120 μL (pH=7.25) and contained 0.8 μmol NPS, 40 μmol Tris HCl and the appropriate amount of enzyme. After 60 minutes of reaction time, 0.5 mL of 1M NaOH was added to the reaction mixture. Released p nitrophenol was determined using a spectrophotometer at 405 nm. In the final step, the IC$_{50}$ parameter values (characterizing the ability of obtained compounds to inhibit steroid sulfatase activity) were determined. For all possible compounds with general formula 1, which are shown in detail in Table 1 as preferred 4-(1-phenyl-1H-[1,2,3]triazol-4-yl)-phenyl sulfamate derivatives, the STS inhibitory activity was observed with IC$_{50}$ values in the range from 0.036 to 0.821 μM. For example, it has been shown that for 4-[1-(3,5-difluoro-phenyl) 1H-[1,2,3]-triazol-4-yl]-phenyl sulfamate IC$_{50}$=0.036 μM, 4-[1-(3-trifluoromethyl-phenyl)-1H-[1,2,3]-triazol-4-yl]-phenyl sulfamate IC$_{50}$=0.180 μM, 4-[1-(4-trifluoromethoxy-phenyl)-1H-[1,2,3]-triazol-4-yl]-phenyl sulfamate IC$_{50}$=0.240 μM, 4-[1-(3,5-Bis-trifluoromethyl-phenyl)-1H-[1,2,3]triazol-4-yl]-phenyl sulfamate IC$_{50}$=0.821 μM. Therefore, the compounds of the general formula 1 have biological, medical and diagnostic activity, and have medical applications for use as a medicament a well as in diagnostics for use as a diagnostic agent. It has been confirmed that the new compounds with general formula 1, as one of the possible mechanisms of medical and biological action, show a strong STS inhibitory activity at low micromolar or nanomolar concentrations, which is sufficient for the compounds to act as drugs classified as steroid sulfatase inhibitors or as compounds for use as steroid sulfatase inhibitors in diagnostic tests, in vitro clinical trials and its use in biological sciences. In particular, the compounds of the general formula 1 are for use as medicaments—useful as drugs in cancer therapy and in particular in the therapy of hormone-dependent cancers of animals, in particular mammals, including humans.

The biological, diagnostics and medical effects of the compounds of the general formula 2 have also been investigated, which are for use as a medicament, in particular estrogen receptor modulators or for use as a diagnostic agent in diagnostic tests in particular as estrogen receptor modulators. The biological use of the compounds in biological sciences in particular in vitro test was also studied. This study was performed by preliminary analysis of the affinity of compounds for estrogen receptors in known in vitro tests. Biological and medical effects of the compounds shown in Table 2 were confirmed.

Due to the fact that the compounds of the general formula 1 can be hydrolyzed to the compounds of the general formula 2, the biological and medical effects of the compounds with general formula 1 are also useful as estrogen receptor modulators or as compounds useful in biological sciences, including diagnostic tests as estrogen receptor modulators. In studies using a standard in vitro test, a high degree of affinity of the compounds with general formula 1 was observed for estrogen receptors.

In the preliminary microbiological tests based on antibiograms, the biological and medical effects of the compounds with general formula 2 were also confirmed. The compounds shown in Table 2 showed inhibition of microbial growth in in vitro tests.

The invention claimed is:

1. Chemical compound that imitate the steroid system and contain a sulfamate moiety, the compound defined by the general formula 1:

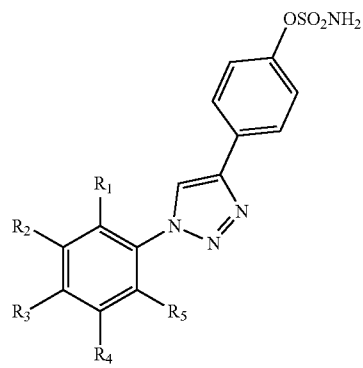

wherein $R_1$=H or F or $CF_3$ or $OCF_3$; $R_2$=H or F or $CF_3$ or Cl or Br or I or $CH_3$ or $OCH_3$ or Et or iPr or $NO_2$; $R_3$=H or F or $CF_3$ or $OCF_3$; $R_4$=H or F or $CF_3$ or Cl or Br or I or $CH_3$ or $OCH_3$; $R_5$=H or F or $CF_3$.

2. A method of treating cancer in a mammal in need thereof, the method comprising administering to the mammal an effective amount of the chemical compound according to claim 1, wherein the cancer is hormone-dependent.

3. An in vitro method of inhibiting steroid sulfatase and/or modulating an estrogen receptor, the method comprising contacting an enzyme with an effective amount of a chemical compound defined by the general formula 1:

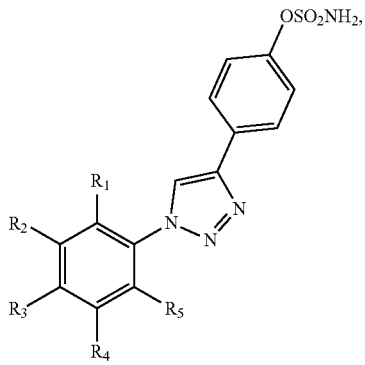

wherein $R_1$=H or F or $CF_3$ or $OCF_3$; $R_2$=H or F or $CF_3$ or Cl or Br or I or $CH_3$ or $OCH_3$ or Et or iPr or $NO_2$; $R_3$=H or F or $CF_3$ or $OCF_3$; $R_4$=H or F or $CF_3$ or Cl or Br or I or $CH_3$ or $OCH_3$, $R_5$=H or F or $CF_3$.

4. Method for the preparation of compound presented by the general formula 1:

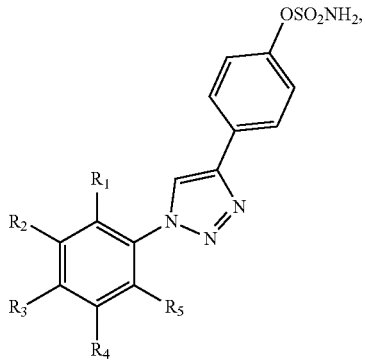

wherein $R_1$=H or F or $CF_3$ or $OCF_3$; $R_2$=H or F or $CF_3$ or Cl or Br or I or $CH_3$ or $OCH_3$ or Et or iPr or $NO_2$; $R_3$=H or F or $CF_3$ or $OCF_3$; $R_4$=H or F or $CF_3$ or Cl or Br or I or $CH_3$ or $OCH_3$; $R_5$=H or F or $CF_3$, while the method is carried out in several steps according to scheme 1:

Step 1

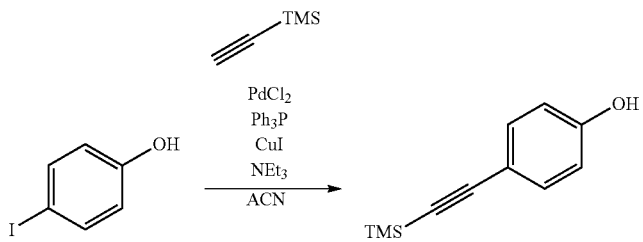

Step 2

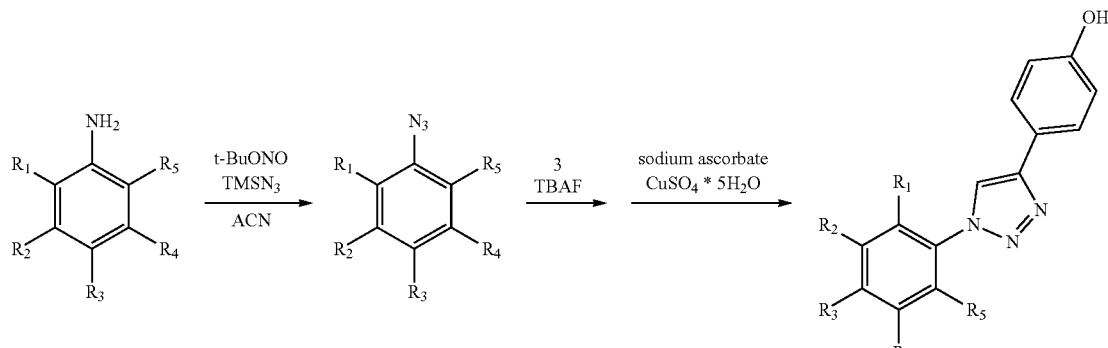

Step 3

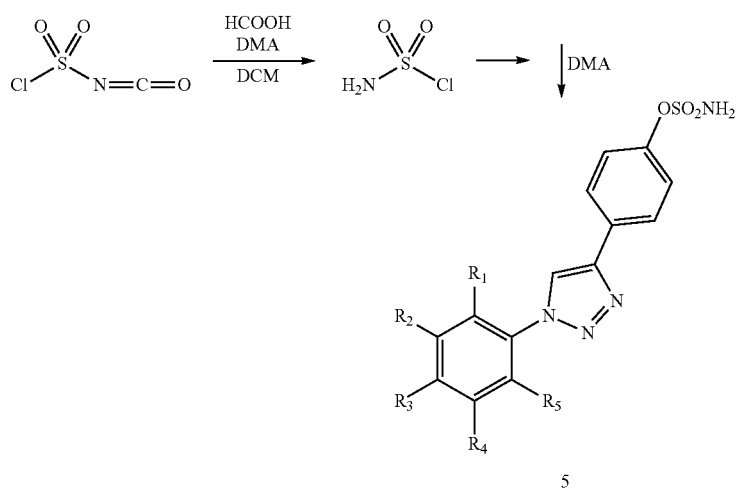

while in the first step, 4-((trimethylsilyl)ethynyl)phenol (3) is obtained by the Sonogashira coupling reaction of p-iodophenol and trimethylsilylacetylene and this step is carried out under reflux, while in the second step, 4-(1-phenyl-1H-[1,2,3]triazol-4-yl)-phenol derivatives are obtained as a result of the 1,3-dipolar cycloaddition reaction of the azide derivative with 4-ethynylphenol or with 4-((trimethylsilyl)ethynyl)phenol (3) in the presence of tetrabutylammonium fluoride (TBAF), and in the third step the final product is obtained by the reaction of sulfamoyl chloride generated in situ with the 4-(1-phenyl-1H-[1,2,3]triazol-4-yl)-phenol derivative (4) and this step is carried out under anhydrous conditions.

5. The method according to the claim 4, wherein the first step is carried out for a minimum of 1 hour.

6. The method according to the claim 4, wherein the second step is carried out at room temperature.

7. The method according to the claim 4, wherein the second step is carried out in situ without isolation or with the isolation of intermediates.

8. The method according to claim 4, wherein the second step is carried out for at least 12 hours.

9. The method according to claim 4, wherein the third step is carried out under anhydrous conditions at a temperature in the range of 15 to 40° C.

10. The method according to claim 4, wherein the third step is carried out for a minimum of 6 hours.

* * * * *